United States Patent
Meola

(10) Patent No.: US 10,828,236 B2
(45) Date of Patent: Nov. 10, 2020

(54) DOSAGE LIMITING DEVICE

(71) Applicant: Paul Meola, St. Petersburg, FL (US)

(72) Inventor: Paul Meola, St. Petersburg, FL (US)

( * ) Notice: Subject to any disclaimer, the term of this patent is extended or adjusted under 35 U.S.C. 154(b) by 0 days.

(21) Appl. No.: 16/556,370

(22) Filed: Aug. 30, 2019

(65) Prior Publication Data

US 2019/0380913 A1  Dec. 19, 2019

Related U.S. Application Data

(63) Continuation-in-part of application No. 16/011,772, filed on Jun. 19, 2018.

(51) Int. Cl.
| | | |
|---|---|---|
| *A61J 7/00* | (2006.01) | |
| *A61M 5/315* | (2006.01) | |
| *A61J 1/18* | (2006.01) | |
| *A61J 1/20* | (2006.01) | |

(52) U.S. Cl.
CPC .............. *A61J 7/0053* (2013.01); *A61J 1/18* (2013.01); *A61J 1/2096* (2013.01); *A61M 5/31525* (2013.01); *A61J 2205/50* (2013.01)

(58) Field of Classification Search
CPC .......... A61M 5/31563; A61M 5/31525; A61M 5/3148; A61M 2005/3125; A61M 2005/3114; A61M 2005/3022; A61M 5/31501; A61M 2005/31508; A61M 5/008; A61M 5/3137; A61M 5/315; A61M 2005/1586; A61M 2005/244; A61M 5/1418; A61M 5/3156; A61M 5/31591; A61M 5/31545; A61M 5/31565; A61M 5/31555; A61M 5/3129; A61J 7/0053; A61J 1/18

See application file for complete search history.

(56) References Cited

U.S. PATENT DOCUMENTS

| | | | | |
|---|---|---|---|---|
| 2,375,711 A | * | 5/1945 | Vondrak .............. | A61M 5/3156 604/210 |
| 2,706,480 A | * | 4/1955 | Nensel .............. | A61M 5/31551 604/211 |
| 2,739,589 A | * | 3/1956 | Yochem ............ | A61M 5/31555 604/210 |
| 2,739,590 A | * | 3/1956 | Yochem ............ | A61M 5/31555 604/210 |
| 3,040,744 A | * | 6/1962 | Hoggard ................. | A61M 5/31 600/578 |
| 3,749,284 A | * | 7/1973 | Kloehn ............. | A61M 5/31591 222/43 |

(Continued)

*Primary Examiner* — Nathan R Price
*Assistant Examiner* — Melissa A Snyder
(74) *Attorney, Agent, or Firm* — Larson & Larson, P.A.; Frank Liebenow; Justin P. Miller

(57) ABSTRACT

An adjustable dosage limiting device is includes an elongated connecting member that has a plunger receiving head at a first end for capturing a plunger flange of a plunger of a syringe. A slidable member having a barrel loop is movable along the elongated connecting member. The slidable member slides up/down the elongated connecting member until, at a preset dosage, a locking mechanism is engaged to lock the slidable member, and hence the barrel loop, in place on the elongated member. Once locked in place, the adjustable dosage limiting device limits a dosage provided by the syringe based upon a distance between the plunger receiving head and the barrel loop as set by the locking mechanism.

17 Claims, 12 Drawing Sheets

(56) References Cited

U.S. PATENT DOCUMENTS

| | | | | |
|---|---|---|---|---|
| 4,153,056 | A * | 5/1979 | Silver | A61M 5/31591 604/211 |
| 4,263,911 | A * | 4/1981 | McCormack | A61M 1/0009 604/227 |
| 5,009,645 | A * | 4/1991 | Silver | A61M 5/3158 604/207 |
| 6,231,550 | B1 * | 5/2001 | Laughlin | A61M 5/3148 604/187 |
| 7,611,495 | B1 * | 11/2009 | Gianturco | A61M 5/31501 604/207 |
| 2007/0225656 | A1 * | 9/2007 | Hoyle, Jr. | A61M 5/2429 604/207 |
| 2013/0090603 | A1 * | 4/2013 | Hoyle, Jr. | A61M 5/3129 604/189 |
| 2015/0196714 | A1 * | 7/2015 | Creaturo | A61M 5/3129 604/198 |
| 2015/0379900 | A1 * | 12/2015 | Samosky | G09B 23/285 434/262 |

* cited by examiner

DOSAGE LIMITING DEVICE

CROSS-REFERENCE TO RELATED APPLICATION

This application is a continuation-in-part of U.S. patent application Ser. No. 16/011,772, filed Jun. 19, 2018.

FIELD

This invention relates to the field of medicine and more particularly to a system for limiting dosages administered by a syringe.

BACKGROUND

It is well known in the art of medicine to administer liquid medication using a syringe. For example, a small child may be given a dosage of 3 ml by way of a plastic syringe. The person or caregiver pushes the plunger of the syringe all the way in, then places the tip of the syringe into the liquid medication, then pulls the plunger out until the base of the plunger aligns with a gradient matching the dosage, or in this example, 3 ml. Then, the tip of the syringe is placed in the mouth of the child and the plunger of the syringe is pushed back in, delivering the requisite amount of the medicine.

Unfortunately, this method of administering a liquid medication (or any liquid) suffers from inaccuracies caused by many reason. For example, the caregiver (or person taking the medication) has poor visibility to the gradients due to darkness or poor eyesight or the caregiver does not understand how to correctly meter the dosage, etc. Due to such inaccuracies, the patient (receiver of the liquid) often is provided with too much of the liquid (medication) or too little.

What is needed is a system that will meter the dosage provided from a syringe to an amount required as preset by a person.

SUMMARY

In one embodiment, an adjustable dosage limiting device is disclosed including an elongated connecting member that has a plunger receiving head at a first end for capturing a plunger flange of a plunger of a syringe. A slidable member is slidably interfaced to the elongated connecting member. The slidable member has a lock that, when engaged, holds the slidable member at a preset location on the elongated connecting member. A barrel loop is connected to the slidable member so that the adjustable dosage limiting device limits a dosage provided by the syringe based upon a distance between the plunger receiving head and the barrel loop as during extraction of the plunger, the barrel loop abuts a barrel flange of the syringe, thereby limiting extraction of the plunger of the syringe.

In another embodiment, a method of limiting a dosage provided by a syringe includes moving a slidable member of an adjustable dosage limiting device along an elongated connecting member until a desired preset dosage limit is set then activating a locking mechanism to fix the slidable member to the elongated connecting member at the desired preset dosage limit. Next, the adjustable dosage limiting device is installed on the syringe by installing a plunger receiving head of the adjustable dosage limiting device on a plunger flange of the syringe (the plunger receiving head at a first end of the elongated connecting member) and installing a barrel loop of the adjustable dosage limiting device around a hollow barrel of the syringe (the barrel loop connected to the slidable member of the elongated connecting member). Now, the plunger flange of the syringe is pushed until the plunger of the syringe is fully within the hollow barrel of the syringe and a hollow tip of the syringe is submerged in a liquid. Now, the plunger flange of the syringe is pulled (extracted) until the barrel loop abuts a barrel flange of the syringe, thereby filling a portion of the hollow barrel of the syringe with the preset amount of the liquid as limited by the adjustable dosage limiting device. The hollow tip is placed into a destination and the plunger flange of the syringe is pushed until the plunger of the syringe is fully within the hollow barrel of the syringe, thereby delivering the preset dosage limited by the adjustable dosage limiting device into the destination.

In another embodiment, an adjustable dosage limiting device is disclosed including an elongated connecting member with a plunger receiving head at a first end for capturing a plunger flange of a plunger of a syringe. The plunger receiving head has a back flange connected to the elongated connecting member and a forward slotted flange connected to the elongated connecting member, the forward slotted flange is separated from the back flange by a space sufficient to accept the plunger flange. A flat section of the plunger fits in a slot of the forward slotted flange. A slidable member is slidably interfaced to the elongated connecting member. The slidable member has a lock that, when engaged, holds the slidable member at a preset location on the elongated connecting member. A barrel loop is connected to the slidable member such that, the adjustable dosage limiting device limits a dosage provided by the syringe based upon a settable distance between the plunger receiving head and the barrel loop as during extraction of the plunger, the barrel loop abuts a barrel flange of the syringe, thereby limiting extraction of the plunger of the syringe.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
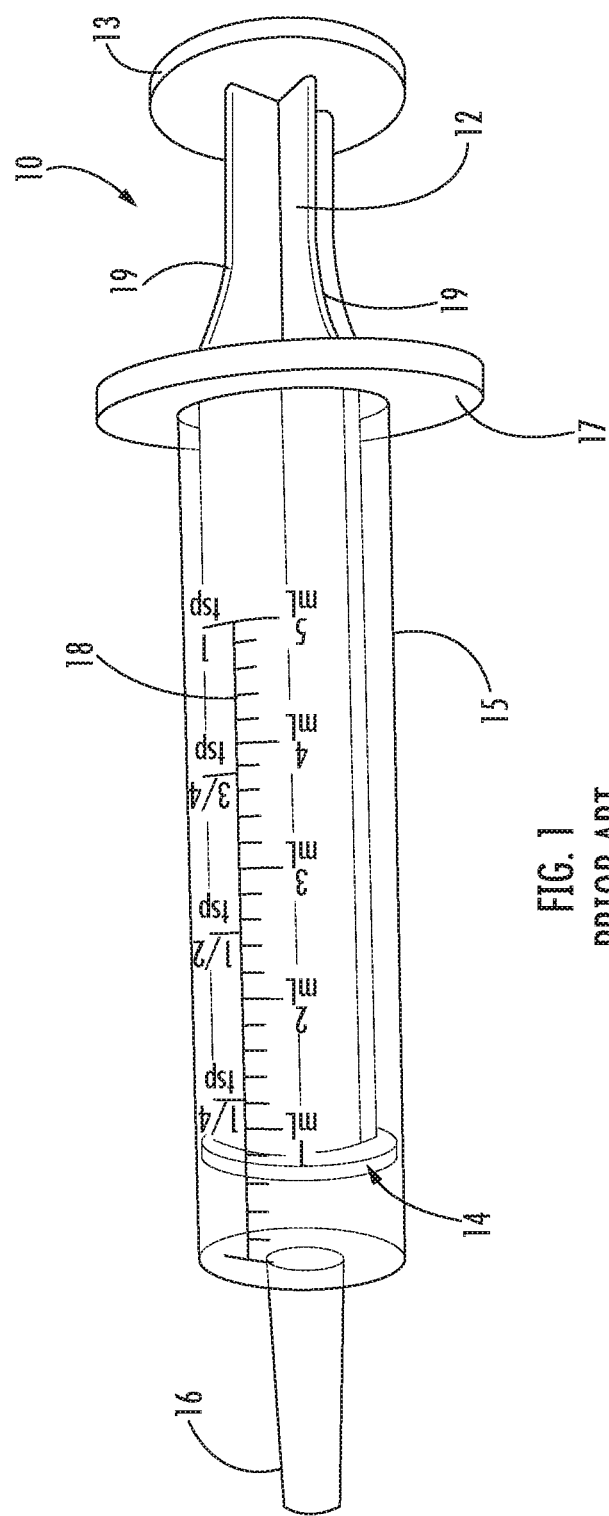
FIG. 1 illustrates a perspective view of a syringe of the prior art.
Figure 2:
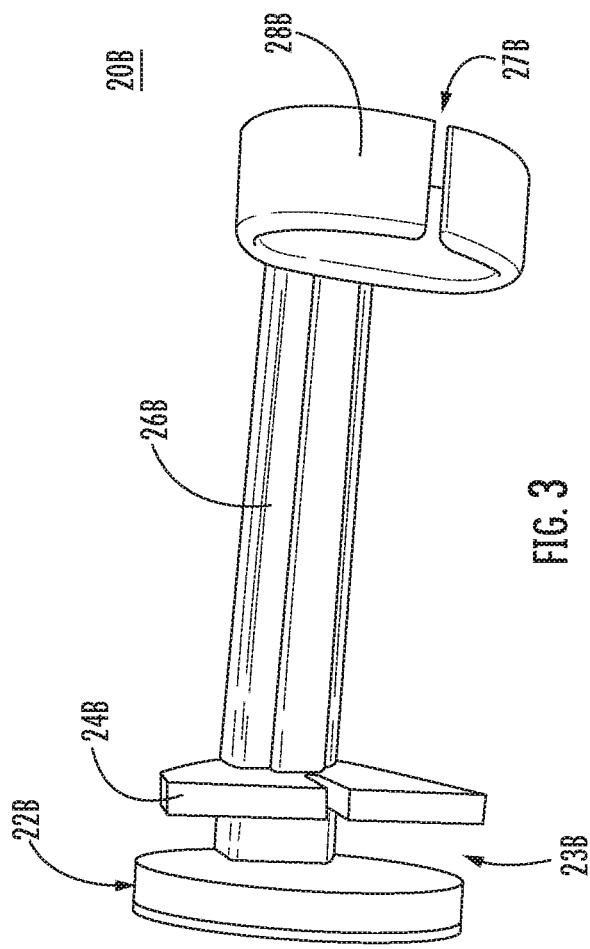
FIG. 2 illustrates a perspective view of a dosage limiting device manufactured for a first dosage amount.
Figure 3:
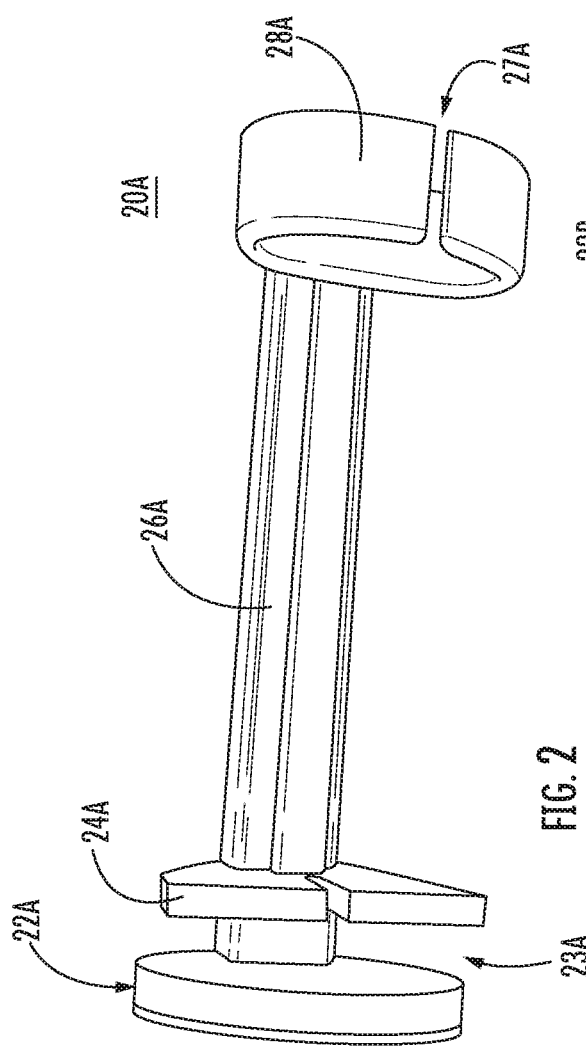
FIG. 3 illustrates a perspective view of a dosage limiting device manufactured for a second dosage amount.
Figure 4:
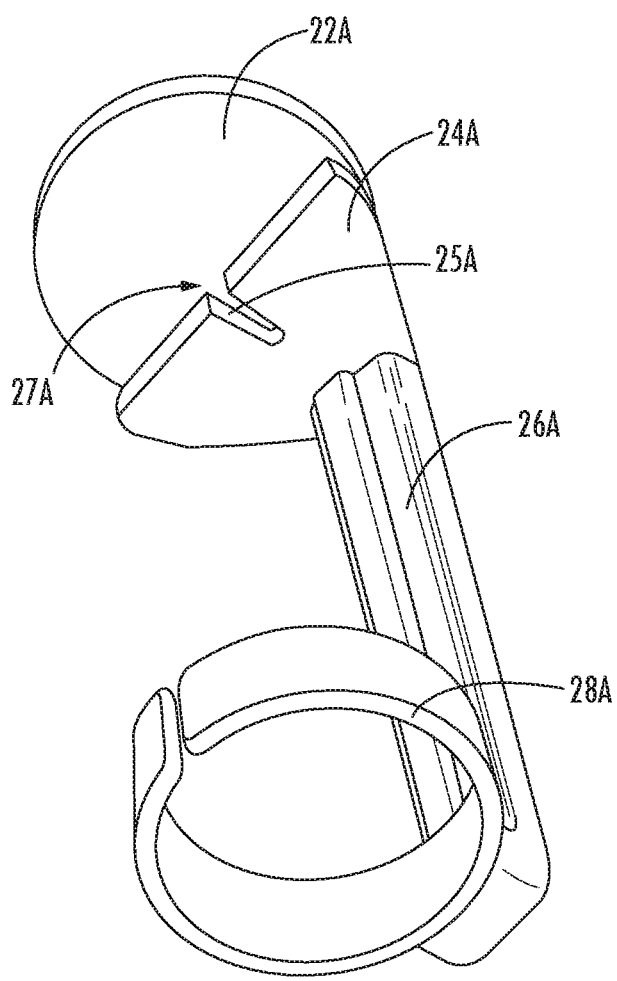
FIG. 4 illustrates a second perspective view of a dosage limiting device manufactured for the first dosage amount.
Figure 5:
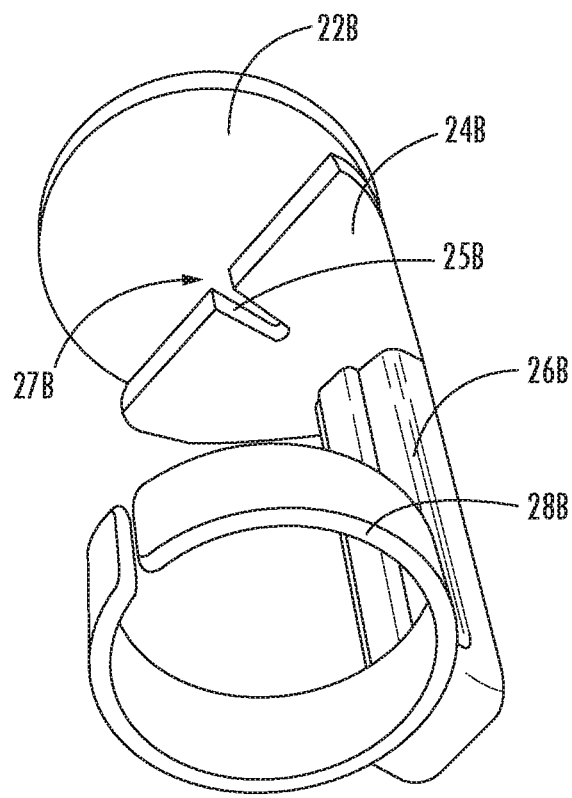
FIG. 5 illustrates a second perspective view of a dosage limiting device manufactured for the second dosage amount.

Reference will now be made in detail to the presently preferred embodiments of the invention, examples of which are illustrated in the accompanying drawings. Throughout the following detailed description, the same reference numerals refer to the same elements in all figures.

Referring to FIG. 1. An exemplary syringe 10 of the prior art is shown. The syringe 10 has a hollow tip 16 for drawing a liquid (e.g. medicine) into the hollow barrel 15 of the syringe 10 and, later, expelling the liquid into a destination (e.g. mouth of the patient). The liquid is drawn into the syringe 10 by first pushing the plunger flange 13 until the plunger seal 14 is all the way into the hollow barrel 15 of the syringe 10, then inserting the hollow tip 16 into the liquid, then pulling the plunger flange 13 out until the plunger seal 14 aligns with a gradient 18 matching the required dosage. To allow finger grips during operation, the syringe 10 has a barrel flange 17. The plunger 12 of a syringe 10 typically has flat sections 19 that improve rigidity.

In practice, syringes 10 provide a range of dosages, in that each typical syringe is capable of providing from a smallest dosage (e.g. 1 ml. or ¼ tsp.) to a largest dosage (e.g. 5 ml. or 1 tsp.).

Referring to FIGS. 2 through 9, two specific dosage limiting devices 20A/20B are shown. Although it is anticipated that dosage limiting devices 20A/20B be provided for any specific dosage, for clarity reasons, only two sizes of dosage limiting devices 20A/20B are shown in the figures and described. It should also be noted that the exact shape and composition of the two, specific dosage limiting devices 20A/20B is not limited as other shapes and materials will accomplish the same or similar function without veering from the disclosure and claims here within.

In FIGS. 2 through 5, the two specific dosage limiting devices 20A/20B are shown from the side. Each dosage limiting device 20A/20B has an elongated connecting member 26A/26B. At a first end of the elongated connecting members 26A/26B is a plunger flange receiving head 22A/24A/22B/24B for capturing a plunger flange 13 of the plunger 12 of the syringe 10. In the example shown, each plunger receiving head 22A/24A/22B/24B consists of a back flange 22A/22B and a forward slotted flange 24A/24B separated by a space 23A/23B wide enough to fit the plunger flange 13 of the plunger 12. The plunger flange 13 fits snuggly in the space between the back flange 22A/22B and a forward slotted flange 24A/24B. As the typical plunger 12 has flat sections 19 that improve rigidity, these flat sections 19 fit into the slot 25A/25B.

At a distal second end of the elongated connecting members 26A/26B is a barrel loop 28A/28B. As shown in FIGS. 6 through 9, in use, the hollow barrel 15 of the syringe 10 is inserted into the barrel loop 28A/28B and the plunger flange 13 of the syringe 10 is inserted into the plunger receiving head 22A/24A/22B/24B. The dosage limiting devices 20A/20B therefore limit the distance that the plunger flange 13 can be extracted from the hollow barrel 15 of the syringe as the barrel loop 28A/28B abuts the barrel flange 17 of the syringe 10.

In some embodiments, each barrel loop 28A/28B has a slit 27A/27B to facilitate capturing the hollow barrel 15 of the syringe 10 within the barrel loops 28A/28B. As one anticipated material from which the dosage limiting devices 20A/20B are made is plastic, by using a pliable and resilient plastic, the barrel loops 28A/28B will open at the slits 27A/27B for ease of installation onto the hollow barrel 15 of the syringe 10.

Note that the length of the elongated connecting member 26A/26B determines the dosage that is administered. For example, the first dosage limiting device 20A has a longer elongated connecting member 26A while the second dosage limiting device 20B has a shorter elongated connecting member 26B.

Figure 6:
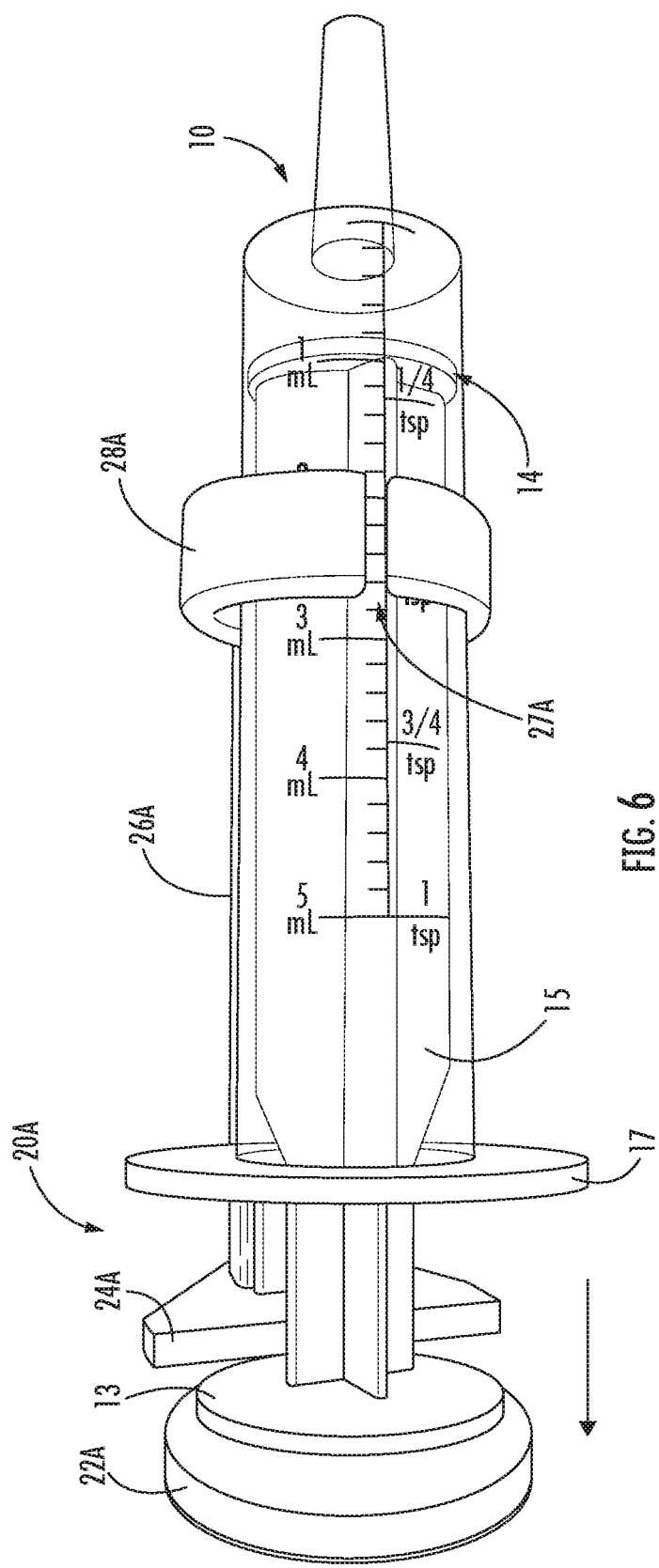
FIG. 6 illustrates a perspective view of a dosage limiting device manufactured for the first dosage amount installed on a syringe with the plunger pushed in all the way.
Figure 7:
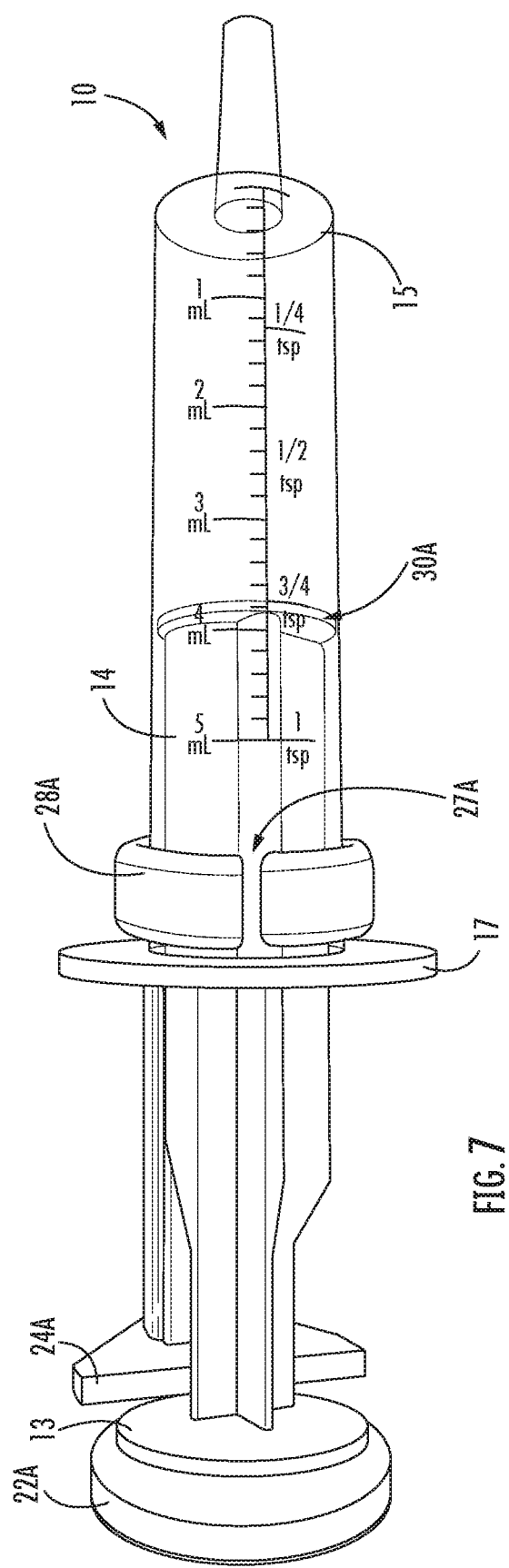
FIG. 7 illustrates a perspective view of a dosage limiting device manufactured for the first dosage amount installed on a syringe with the plunger pulled out as far as allowed by the dosage limiting device.

Operation of the dosage limiting devices 20A/20B are shown in FIGS. 6-9. In FIG. 6, the first dosage limiting device 20A mounted on the syringe 10 with the plunger 12 of the syringe 10 pushed in. In FIG. 7, the first dosage limiting device 20A is shown limiting how far the plunger 12 of the syringe 10 can be pulled out. In this example, when the plunger 12 of the syringe 10 is pulled out, the first dosage limiting device 20A limits extraction to the ¾ tsp. gradient 30A, therefore, in this example, the first dosage limiting device 20A limits the dosage to ¾ tsp.

Figure 8:
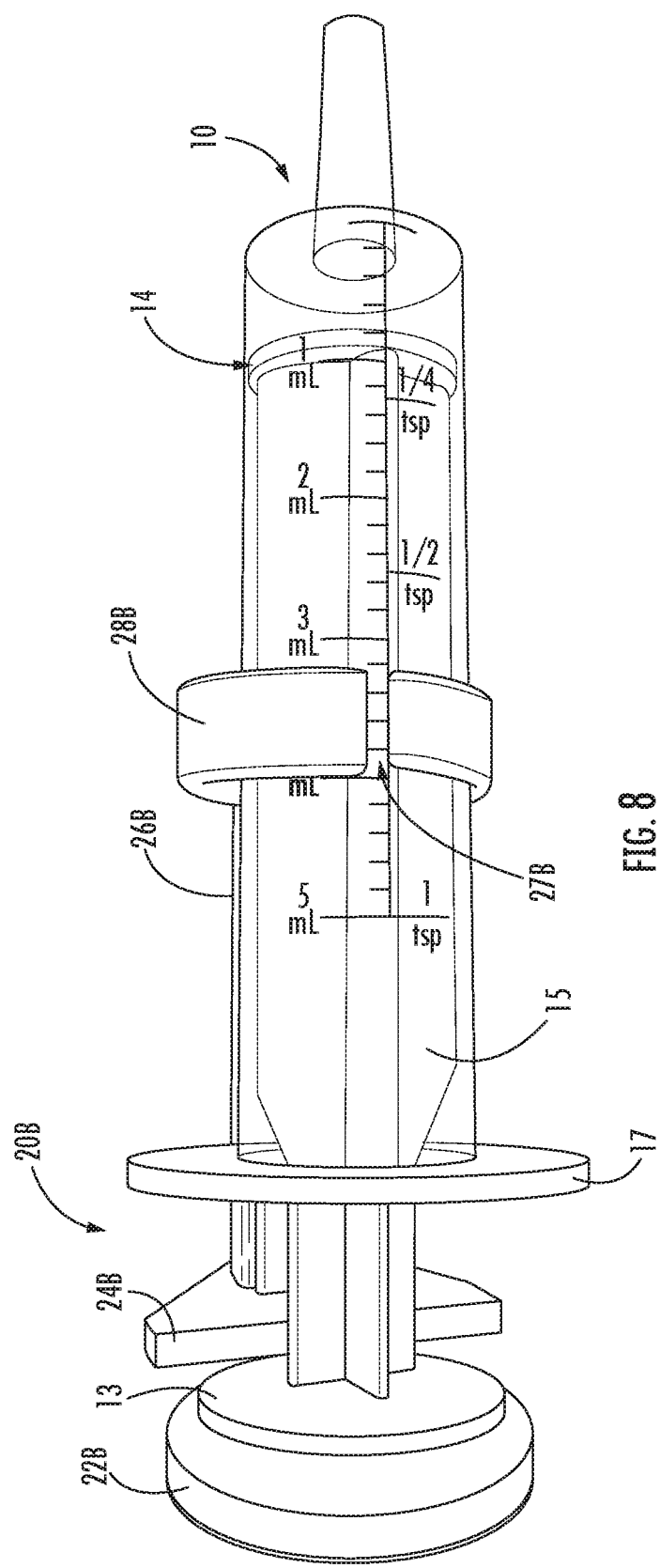
FIG. 8 illustrates a perspective view of a dosage limiting device manufactured for the second dosage amount installed on a syringe with the plunger pushed in all the way.
Figure 9:
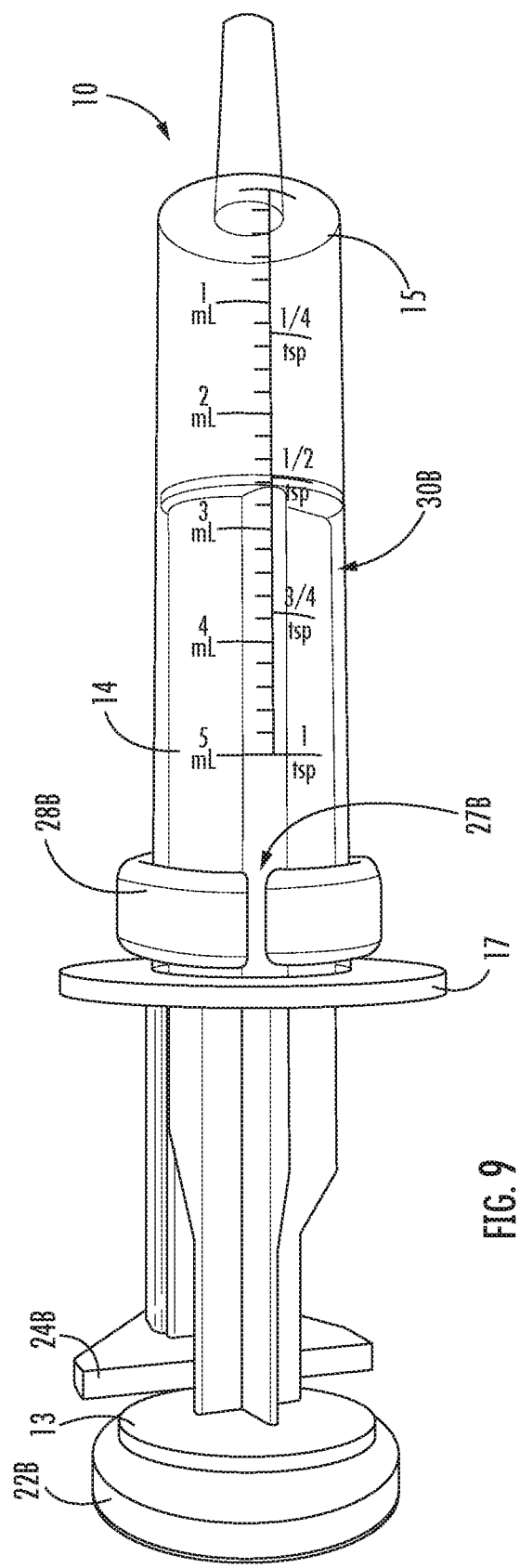
FIG. 9 illustrates a perspective view of a dosage limiting device manufactured for the second dosage amount installed on a syringe with the plunger pulled out as far as allowed by the dosage limiting device.
Figure 10:
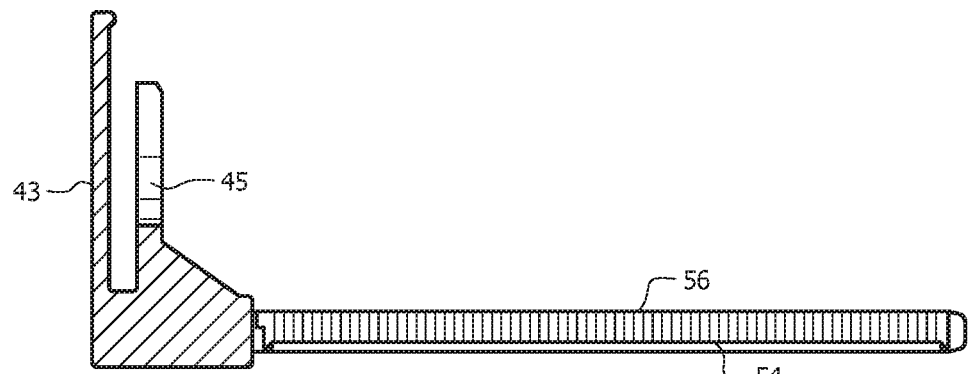
FIG. 10 illustrates a sectional view of an elongated member of a settable dosage limiting device.
Figure 11:
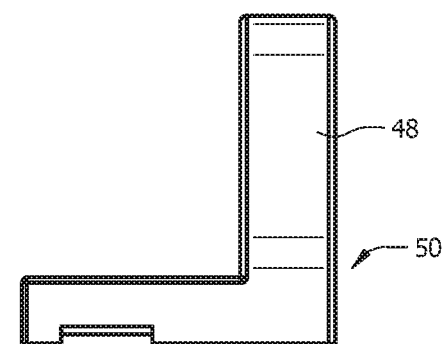
FIG. 11 illustrates a plan view of a barrel-capture and locking member of the settable dosage limiting device.
Figure 12:
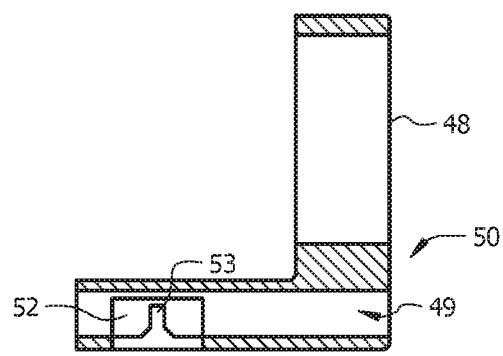
FIG. 12 illustrates a sectional view of a barrel-capture and locking member of the settable dosage limiting device.
Figure 13:
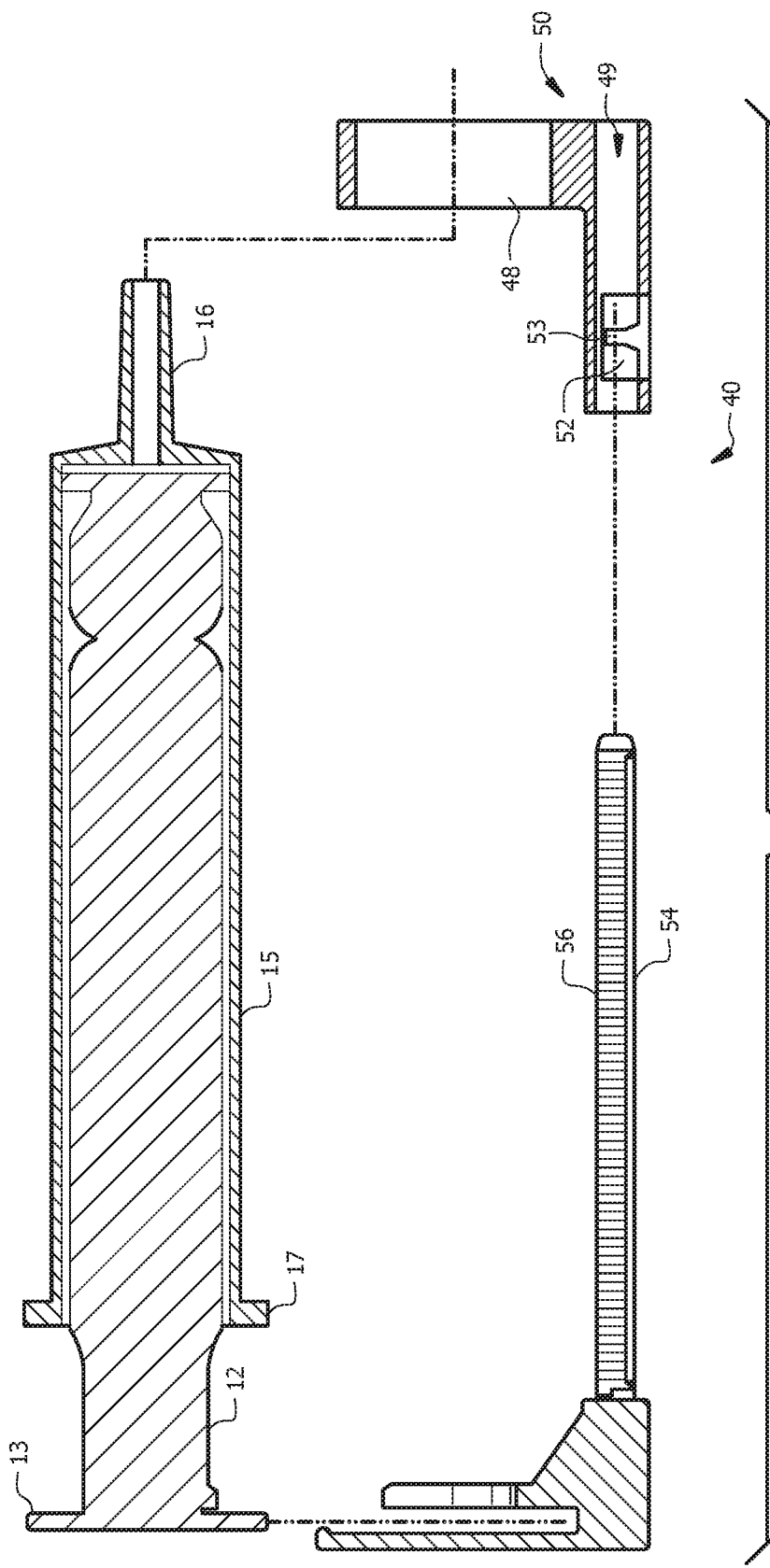
FIG. 13 illustrates an exploded sectional view of a syringe and the settable dosage limiting device.
Figure 14:
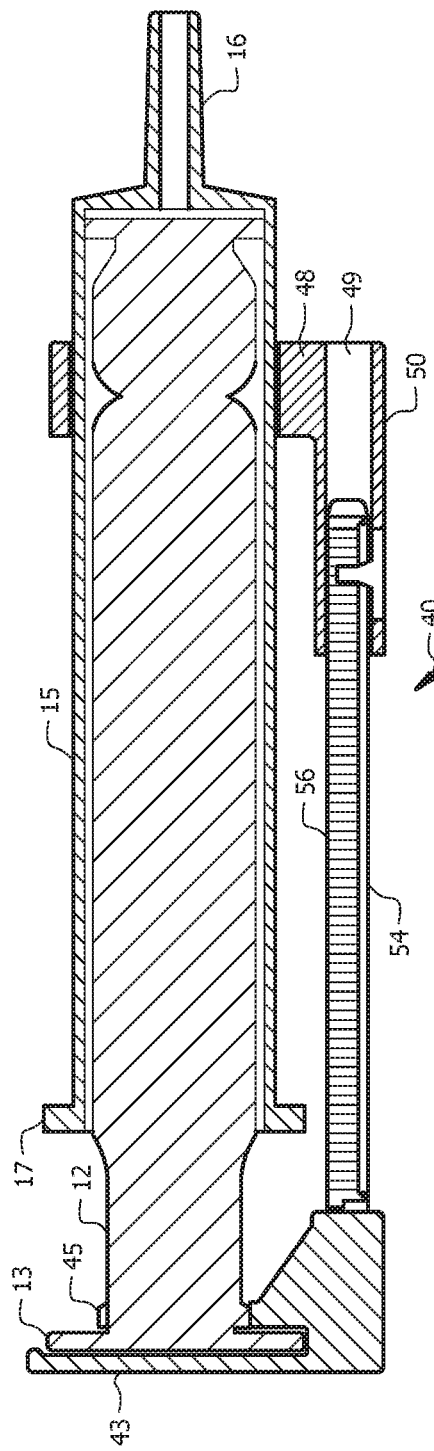
FIG. 14 illustrates a sectional view of the settable dosage limiting device installed on the syringe.
Figure 15:
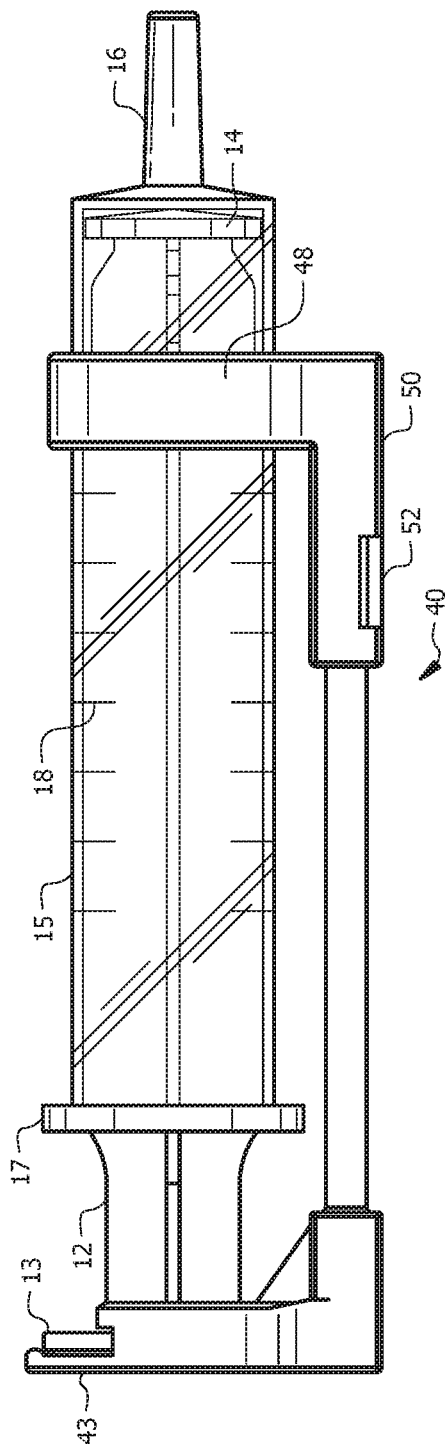
FIG. 15 illustrates an elevational view of the settable dosage limiting device installed on the syringe.
Figure 16:
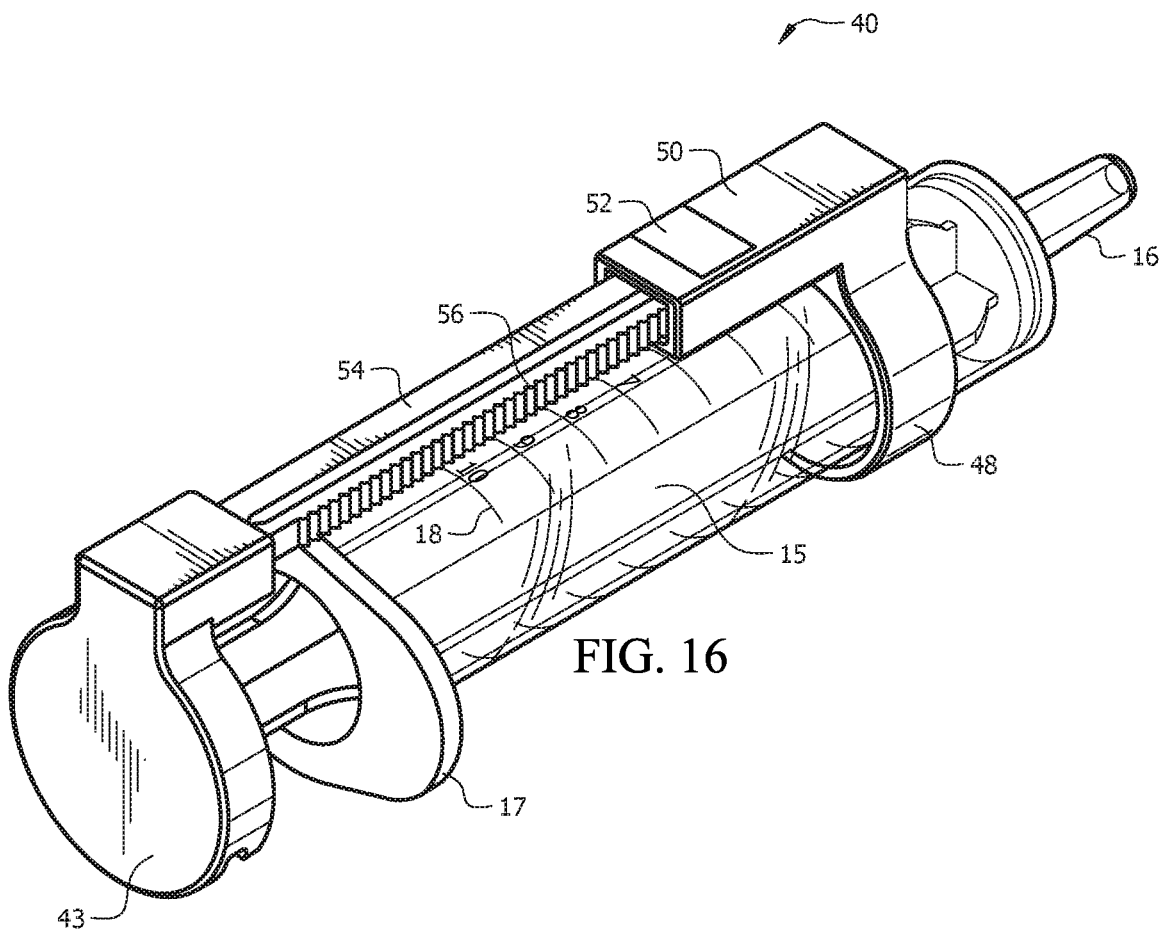
FIG. 16 illustrates a perspective view of the settable dosage limiting device preset for a dosage amount and installed on a syringe with the plunger of the syringe pushed all the way into the syringe.
Figure 17:
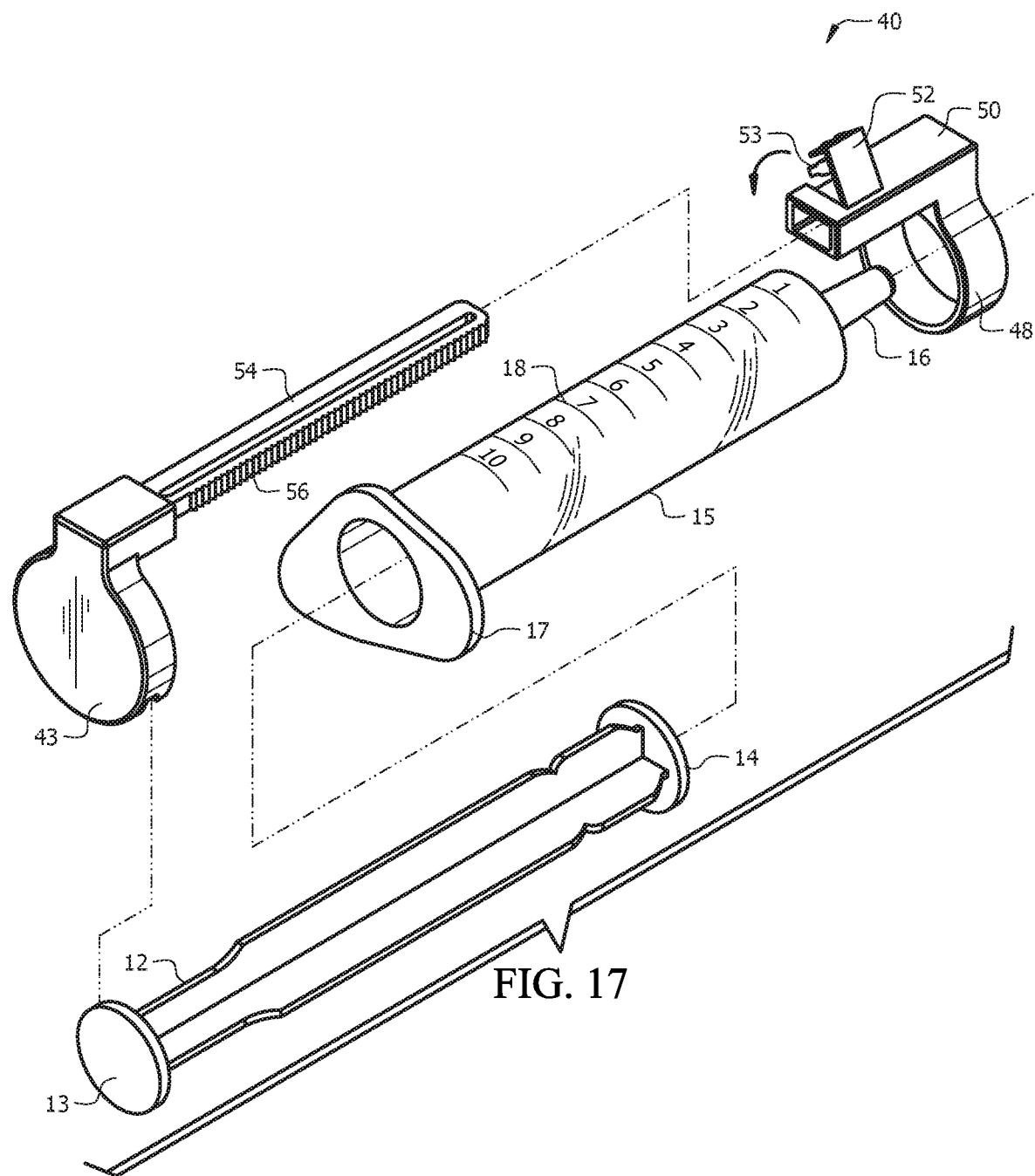
FIG. 17 illustrates a perspective view of the settable dosage limiting device and the syringe.

Now, in FIG. 8, the second dosage limiting device 20B is mounted on the syringe 10 with the plunger 12 of the syringe 10 pushed in. In FIG. 9, the second dosage limiting device 20B is shown limiting how far the plunger 12 of the syringe 10 can be pulled out. In this example, when the plunger 12 of the syringe 10 is pulled out, the second dosage limiting device 20B limits extraction to the ½ tsp. gradient 30B, therefore, in this example, the second dosage limiting device 20B limits the dosage to ½ tsp.

Again, the two dosage limiting devices 20A/20B are examples and it is fully anticipated that dosage limiting devices 20A/20B be provided for various sizes of syringes and for any desired dosage in metric (e.g. ml) or English units (e.g. tsp.).

It is fully anticipated that the dosage limiting devices 20A/20B be provided as single items or in packages containing several, either having all the same dosage amounts or different dosage amounts. For example, a package of five dosage limiting devices 20A/20B contains one each dosage limiting device 20A/20B or 1 ml, 2 ml, 3 ml, 4 ml, and 5 ml. It is also anticipated that, in some embodiments, each dosage limiting devices 20A/20B be marked with markings indicating the dosage of such and, in some embodiments a company advertisement is also marked on the dosage limiting devices 20A/20B (e.g., a pharmacy name).

Referring to FIGS. 10-17, an adjustable dosage limiting device 40 is shown. The dosage limiting device 20A/20B described above works fine for fixed dosages, each dosage limiting device 20A/20B limiting dosages to a fixed amount and each one calibrated at manufacture to a fixed limit.

These types of fixed dosage limiting devices require, in some applications, a pharmacy (for example) to stock several types of dosage limiting devices 20A/20B. Instead of stocking several dosage limiting devices 20A/20B, one for each anticipated dosage, the adjustable dosage limiting device 40 provides for a settable range of dosage limits. In such, a pharmacist (for example) presets the adjustable dosage limiting device 40 to the proper dosage for the patient. After presetting the adjustable dosage limiting device 40 and installing the adjustable dosage limiting device 40 onto the syringe 10, the adjustable dosage limiting device 40 prevents the plunger flange 13 of the syringe 10 from being withdrawn by more than the preset dosage.

Although the adjustable dosage limiting device 40 shown in FIGS. 10-17 has a specific locking mechanism, any similar or different locking mechanism is equally anticipated and included here within.

Therefore, the exemplary adjustable dosage limiting device 40 includes a barrel loop 48 that, when installed, surrounds the hollow barrel 15 (e.g. when no medication is present) of the syringe 10. The barrel loop 48 is connected to or part of a sliding member 50 that, until locked, slides up/down the elongated shafts 54/56. After the locking mechanism 52/53 is closed (locked position) the sliding member 50 becomes stationary along the elongated shafts 54/56. The elongated shafts 54/56 fit within and slide through a space 49 between inner surfaces of the sliding member 50.

In the locked position, the tab 52 of the locking mechanism 52/53 is flush or recessed into a surface of the sliding member 50 so that the locking mechanism 52/53 is not easily defeated. Also, in the locked position, the wedge 53 of the locking mechanism 52/53 is inserted between the elongated shafts 54/56, thereby exerting pressure between the elongated shafts 54/56 and inner surfaces of the sliding member 50.

At an end of the elongated shafts 54/56 that is distal from the sliding member 50, there is a receiving head 43/45. The receiving head 43/45 captures the plunger flange 13, so that, as the plunger flange 13 is pulled to draw a fluid into the hollow barrel 15 of the syringe 10, the elongated shafts 54/56 pull the sliding member 50 and barrel loop 48 along the hollow barrel 15 of the syringe 10 until the barrel loop 48 abuts the barrel flange 17 of the syringe 10, thereby limiting how far the plunger flange 13 can be extracted and, therefore, the amount of liquid (medication) that is drawn into the hollow barrel 15. In this way, the pharmacist (for example) is able to set a predetermined maximum dosage using the adjustable dosage limiting device 40 so that a patient will administer a proper dosage and not provide a dosage that is more than preset (prescribed).

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An adjustable dosage limiting device comprising:
an elongated connecting member;
a plunger receiving head for capturing a plunger flange of a plunger of a syringe, the plunger receiving head is at a first end of the elongated connecting member;
a slidable member slidably interfaced to the elongated connecting member, the slidable member having a lock, the lock, when engaged, holding the slidable member at a preset location on the elongated connecting member; and
a barrel loop fixedly connected to the slidable member, the barrel loop for freely sliding across a barrel of the syringe; and
whereas the adjustable dosage limiting device limits a dosage provided by the syringe based upon a distance between the plunger receiving head and the barrel loop as during extraction of the plunger, the barrel loop abuts a barrel flange of the syringe, thereby limiting extraction of the plunger of the syringe.

2. The adjustable dosage limiting device of claim 1, wherein the plunger receiving head has a back flange connected to the elongated connecting member and a forward slotted flange connected to the elongated connecting member so that a slot of the slotted flange is adjacent to the elongated member, the forward slotted flange is separated from the back flange by a space sufficient to accept the plunger flange, a flat section of the plunger fitting in a slot of the forward slotted flange.

3. The adjustable dosage limiting device of claim 1, wherein the barrel loop is tubular to surround a hollow barrel of the syringe.

4. The adjustable dosage limiting device of claim 3, wherein the barrel loop has a slit for ease of installation on the hollow barrel of the syringe.

5. The adjustable dosage limiting device of claim 1, further comprising markings on the elongated connecting member.

6. The adjustable dosage limiting device of claim 5, wherein the markings include an advertisement.

7. A method of limiting a dosage provided by a syringe, the method comprising:
first, installing the adjustable dosage limiting device on the syringe by:
installing a plunger receiving head of the adjustable dosage limiting device on a plunger flange of the syringe, the plunger receiving head at a first end of the elongated connecting member;
installing a barrel loop of the adjustable dosage limiting device around a hollow barrel of the syringe, the barrel loop connected to the slidable member of the elongated connecting member;
pushing the plunger flange of the syringe until the plunger of the syringe is fully within the hollow barrel of the syringe;
second, moving a slidable member of an adjustable dosage limiting device along an elongated connecting member until a desired preset dosage limit is set;
third, activating a locking mechanism to fix the slidable member to the elongated connecting member at the desired preset dosage limit after which, the slidable member is locked to the elongated connecting member;
fourth, submerging a hollow tip of the syringe into a liquid;
fifth, pulling the plunger flange of the syringe until the barrel loop abuts a barrel flange of the syringe, thereby filling a portion of the hollow barrel of the syringe with the liquid to the preset amount of the liquid as limited by the adjustable dosage limiting device;

sixth, placing the hollow tip into a destination; and seventh, pushing the plunger flange of the syringe until the plunger of the syringe is fully within the hollow barrel of the syringe, thereby delivering the preset dosage limited by the adjustable dosage limiting device into the destination.

8. The method of claim 7, wherein the plunger receiving head has a back flange connected to the elongated connecting member and a forward slotted flange connected to the elongated connecting member, forward slotted flange is separated from the back flange by a space sufficient to accept the plunger flange, a flat section of the plunger fitting in a slot of the forward slotted flange.

9. The method of claim 7, wherein the barrel loop of the adjustable dosage limiting device is tubular to surround the hollow barrel of the syringe.

10. The method of claim 9, wherein the barrel loop has a slit for ease of installation on the hollow barrel of the syringe.

11. The method of claim 7, further comprising markings on the elongated connecting member of the adjustable dosage limiting device.

12. The method of claim 11, wherein the markings include an advertisement.

13. An adjustable dosage limiting device comprising:
an elongated connecting member;
a plunger receiving head for capturing a plunger flange of a plunger of a syringe, the plunger receiving head is at a first end of the elongated connecting member, the plunger receiving head has a back flange connected to the elongated connecting member and a forward slotted flange connected to the elongated connecting member, the forward slotted flange is separated from the back flange by a space sufficient to accept the plunger flange, a flat section of the plunger fitting in a slot of the forward slotted flange;
a slidable member slidably interfaced to the elongated connecting member, the slidable member having a lock, the lock, when engaged, holding the slidable member at a preset location on the elongated connecting member; and
a barrel loop directly connected to the slidable member, the barrel loop for freely sliding across a barrel of the syringe;
whereas the adjustable dosage limiting device limits a dosage provided by the syringe based upon a settable distance between the plunger receiving head and the barrel loop as during extraction of the plunger, the barrel loop abuts a barrel flange of the syringe, thereby limiting extraction of the plunger of the syringe.

14. The adjustable dosage limiting device of claim 13, wherein the barrel loop is tubular to surround a hollow barrel of the syringe.

15. The adjustable dosage limiting device of claim 14, wherein the barrel loop has a slit for ease of installation on the hollow barrel of the syringe.

16. The adjustable dosage limiting device of claim 13, further comprising markings on the elongated connecting member.

17. The adjustable dosage limiting device of claim 16, wherein the markings include an advertisement.

* * * * *